(12) United States Patent
Akerfeldt et al.

(10) Patent No.: US 6,786,915 B2
(45) Date of Patent: Sep. 7, 2004

(54) REINFORCED ABSORBABLE MEDICAL SEALING DEVICE

(75) Inventors: Dan Akerfeldt, Uppsala (SE); Fredrik Preinitz, Uppsala (SE); Per Egneloev, Uppsala (SE); Torbjoern Mathisen, Alvsjo (SE)

(73) Assignee: Radi Medical Systems AB, Uppsala (SE)

( * ) Notice: Subject to any disclaimer, the term of this patent is extended or adjusted under 35 U.S.C. 154(b) by 42 days.

(21) Appl. No.: 10/124,725

(22) Filed: Apr. 18, 2002

(65) Prior Publication Data
US 2002/0198562 A1 Dec. 26, 2002

Related U.S. Application Data

(63) Continuation of application No. 09/836,529, filed on Apr. 18, 2001, now Pat. No. 6,596,012.
(60) Provisional application No. 60/204,118, filed on May 15, 2000.

(30) Foreign Application Priority Data

Apr. 19, 2000 (EP) ............................................. 00850069

(51) Int. Cl.⁷ ............................................. A61B 17/04
(52) U.S. Cl. ...................................... 606/232; 606/213
(58) Field of Search ................................. 606/213, 215, 606/232, 233, 158, 214, 216, 217, 221, 151; 623/1.38

(56) References Cited

U.S. PATENT DOCUMENTS

| 3,447,553 A | * | 6/1969 | Spicer ......................... 600/32 |
|---|---|---|---|
| 4,744,364 A | | 5/1988 | Kensey |
| 4,852,568 A | | 8/1989 | Kensey |
| 4,890,612 A | | 1/1990 | Kensey |
| 5,021,059 A | | 6/1991 | Kensey et al. |
| 5,192,302 A | | 3/1993 | Kensey et al. |
| 5,342,393 A | | 8/1994 | Stack |
| 5,350,399 A | | 9/1994 | Erlebacher et al. |
| 5,531,759 A | | 7/1996 | Kensey et al. |
| 5,545,178 A | * | 8/1996 | Kensey et al. .............. 606/213 |
| 5,620,461 A | | 4/1997 | Muijs Van De Moer et al. |
| 5,725,577 A | | 3/1998 | Saxon |
| 5,861,004 A | | 1/1999 | Kensey et al. |
| 6,241,768 B1 | * | 6/2001 | Agarwal et al. ......... 623/11.11 |
| 6,290,708 B1 | * | 9/2001 | Kugel et al. ................. 606/151 |
| 6,596,012 B2 | * | 7/2003 | Akerfeldt et al. ........... 606/213 |
| 2002/0019648 A1 | | 2/2002 | Akerfeldt et al. |
| 2003/0114552 A1 | * | 6/2003 | Schacht ..................... 523/113 |

FOREIGN PATENT DOCUMENTS

| EP | 0 766 947 | 4/1997 |
|---|---|---|
| EP | 0 894 475 | 2/1999 |
| EP | 1 147 743 A1 | 10/2001 |
| WO | WO 90/14796 A1 | 12/1990 |
| WO | WO 94/28800 A1 | 12/1994 |

OTHER PUBLICATIONS http://ecal–admin.mme.tcd.ie/MSEInteractive/tb02.pdf.*
Derwent–Acc–No: 1990–068442.*

* cited by examiner

Primary Examiner—Julian W. Woo
Assistant Examiner—D. Jacob Davis
(74) Attorney, Agent, or Firm—Foley & Lardner LLP

(57) ABSTRACT

The present invention provides a medical sealing device having a decreased risk that a fastening means, such as a suture or a multifilament, ruptures through the sealing device. An absorbable medical sealing device (3; 10; 15) according to the present invention is provided with one or more recesses (6, 7; 13; 18) for fastening means (5; 14; 17) and is characterized in that the sealing device (3; 10; 15) comprises a base portion (8; 11; 16), which is made of a first material having a lower modulus, and a reinforcement portion (9; 12; 19), which is made of second material having a higher modulus, the reinforcement portion (9; 12; 19) being provided to reinforce said recesses (6, 7; 13; 18).

12 Claims, 2 Drawing Sheets

REINFORCED ABSORBABLE MEDICAL SEALING DEVICE

CROSS-REFERENCE TO RELATED PATENT APPLICATIONS

This application is a Continuation in Part of U.S. application Ser. No. 09/836,529, filed Apr. 18, 2001, now U.S. Pat. No. 6,596,012, incorporated herein by reference in its entirety. The Inventors hereby claim the benefit of priority of U.S. application Ser. No. 09/836,529; U.S. Application No. 60/204,118, filed May 15, 2000, incorporated herein by reference in its entirety; and European Application 00850069.6, filed Apr. 19, 2000, incorporated herein by reference in its entirety.

FIELD OF THE INVENTION

The present invention relates generally to the field of sealing devices for the sealing of a percutaneous puncture in a vessel. The invention relates particularly to an absorbable or bioabsorbable sealing device being provided with recesses for fastening means, which sealing device is made of a first material having a lower rupture strength and a second material having a higher rupture strength, the second material being arranged to reinforce the recesses in the sealing device.

BACKGROUND OF THE INVENTION

During certain types of medical surgery or treatment, an introducer is used to access the vascular system of a patient. The introducer is inserted through the wall of a blood vessel in order to obtain access to the vascular system and may thereafter be used for guiding medical instruments such as catheters, guide wires and the like.

After completion of the medical procedure, there will be an incision or a wound in the wall of the blood vessel corresponding to the size of the introducer. The bleeding from the wound, which is a result of such a surgical operation, can be stopped by applying direct pressure on the wound. However, applying direct pressure on the wound will require assistance of medical personnel and may also restrict the flow of blood through the vessel.

EP 766 947 A2 describes a haemostatic puncture device for sealing a percutaneous puncture. The entire contents of this EP publication are incorporated herein by reference. The main parts of this device are an anchoring means, a collagen foam acting as a sealing means, a filament means and a carrier means. The device uses an introducer or the like in order to guide the different parts to the puncture. The anchoring means, which is a narrow, rigid beam member, is introduced through the puncture to be inserted into the vessel. During the introduction, the anchoring means is in a longitudinal position in order to fit into the introducer. To function as an anchor, the anchoring means is manipulated in such a way that its end portions grip the inner edges of the puncture. The anchoring means is connected to the sealing means by the filament means in a pulley-like configuration. Thus, after the anchoring means has been put in place and the introducer has been withdrawn, the pulley-like configuration will pull the sealing means towards the puncture and eventually seal the puncture on the outside wall of the vessel. Thus, the collagen foam performs all the sealing, i.e. the puncture is only sealed on the outside wall of the vessel. The collagen foam is effective in stopping the flow of blood through the puncture wound, but the closure device according to EP 766 947 A2 has disadvantages. Besides the risk that the local tension applied to the edges of the puncture by the anchoring means will rupture the edges of the puncture, there is a potential risk that the tension in the filament means will cause the filament means to rupture through the anchoring means, thereby leaving the anchoring means loose inside the vessel. Furthermore, the use of a sealing device that seals on the outside of the vessel only enhances this potentially severe problem, because an outer sealing requires higher sealing force, i.e. higher tension in the filaments means, than a corresponding inner sealing.

Another sealing device is disclosed in U.S. Pat. No. 4,852,568. The entire contents of this US Patent are incorporated herein by reference. This device comprises a retraction filament fixedly secured to a plug means to be introduced into the vessel by an introducer means. When the plug means, which is made of a material being absorbable by the body, has been introduced into the vessel, the retraction filament is pulled until the engagement surface of the plug means is in intimate engagement with the interior of the artery wall. In order to hold the closure in place, the filament is held taut and is secured in position on the patient's skin, such as by use of a strip of conventional tape. Unlike the sealing means disclosed in EP 766 947 A2, the plug means according to U.S. Pat. No. 4,852,568 seals the puncture on the inside of the vessel wall. However, the risk that the fastening means, in this case a filament, which must be pulled with considerable force and which is then left tightened for a time period being as long as several days or even weeks, ruptures through the plug means is still present. Especially when, as pointed out in the application, the filament consists of a very thin thread this risk appears to be significant. Furthermore, the risk is enhanced by the fact that the plug means according to U.S. Pat. No. 4,852,568 is made of an absorbable (e.g. biodegradable) material that also is resilient (a preferred material according to U.S. Pat. No. 4,852,568 is Gelfoam, a porous, absorbable gelatin sold by Johnson & Johnson, Inc.) since such materials usually are known to have low rupture strength.

Through U.S. Pat. No. 5,350,399 is disclosed another sealing device for sealing a puncture in the wall of a blood vessel. This sealing device comprises an intra-arterial occluder and an extra-arterial occluder, which, in a sealing position, are held together by a guide means being integral with and extending centrally from the intra-arterial occluder. According to U.S. Pat. No. 5,350,399, the guide means, which can be in the form of an elongated flexible wire, as well as the occluders can be made of a bioabsorbable material. Further, each occluder is formed of a material and a shape so as to be circumferentially collapsible from a normal position, and should be resiliently expandable from the collapsed state to the normal position. As stated above, bioabsorbable materials having these properties are often characterized by having low rupture strength, and the risk that the fastening means, in this case in the form of a guide means, will rupture through the intra-arterial occluder is still present.

In this context, it should be noted that the problem that an inner seal, i.e. a sealing member designed to be positioned against the inner wall of a blood vessel, will come loose in the artery has severe implications both on long and short terms. If the fastening means ruptures through the inner seal during the introduction or shortly after its introduction, i.e. before haemostasis is obtained, the immediate problem is, of course, to stop the flow of blood through the puncture wound. For this incident, when a sealing operation is carried out using this type of intra-arterial occluder, a device for applying external compression pressure on the puncture site is often kept prepared as a precaution. If, however, the fastening means ruptures through the inner seal when haemostasis already is obtained, the problem is that the inner seal can follow the flow of blood to a position where the artery is so narrow that the inner seal occludes the blood vessel, which may necessitate amputation of the part of the body in which the inner seal has got stuck. Having in mind that it normally takes several months before the body actually absorbs arterial sealing devices being made of absorbable material, it is easy to realize that the long-term requirements regarding the rupture strength of such sealing devices are quite severe.

It should also be noted that a requirement for an intra-arterial sealing device is that it is resilient, since it usually has to be folded, collapsed or in some other way deformed in order to fit in some kind of introducer means before the introduction through the puncture hole and into the vessel. When positioned inside the vessel, the sealing device is unfolded or expanded so as to seal the puncture in the vessel wall. Or, with other words, the diameter of the sealing device must be smaller than the diameter of the puncture hole in the introduction phase, whereas the diameter of the sealing device must be larger than the diameter of the puncture hole in the sealing phase. Generally speaking, the problem is that absorbable (e.g. biodegradable) materials having these properties, i.e. being characterized by having a low modulus, usually also are characterized by having low rupture strength. The rupture strength referred to herein relates to the force needed to displace an implanted object, which is fixed by some fastening means, such as sutures, filaments, screws or other fasteners used to fix the object in position relative to the surrounding soft or hard tissue, or the force needed to displace the fastening means once stitched through the implanted object. The rupture strength of a material is related to the modulus (commonly also referred to as the elastic modulus or Young's modulus) of the material, so that a low modulus material is characterized by having low rupture strength. A high modulus material has a higher resistance to force.

Thus there is a need in the art for an improved arterial sealing device that provides safe sealing of a percutaneous puncture and at the same time reduces the risk that a fastening means connected to the sealing devices ruptures through the absorbable material such that sealing device come loose inside the artery.

SUMMARY OF THE INVENTION

The present invention overcomes the problems of low rupture strength often encountered in arterial sealing devices made of absorbable materials by incorporating areas with increased tensile properties in a device made from such low modulus materials. The invention discloses how a high modulus material can be used to reinforce recesses provided in a sealing device for engagement with the fastener so that the risk that the fastener will rupture through said recesses is obviated or at least minimized.

DETAILED DESCRIPTION OF THE PREFERRED EMBODIMENTS

Figure 1:
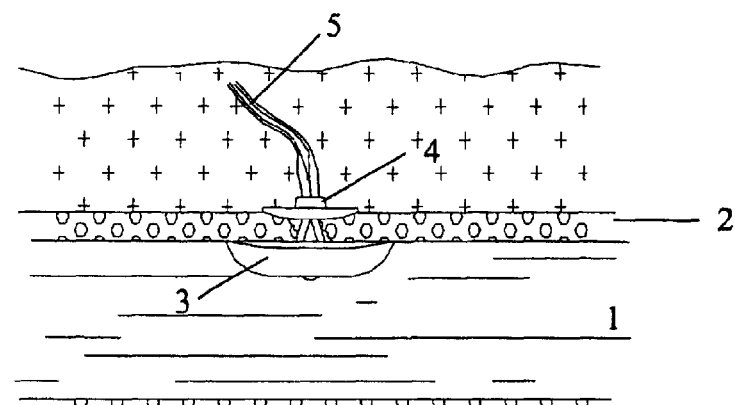
FIG. 1 is a schematic cross-sectional view of a first embodiment of an inventive wound closure device implanted in a sealing position around a vessel.

In order to effectively seal an arterial puncture wound, an absorbable sealing device for intra-arterial sealing should preferably be made of a material that is characterized by being soft and flexible, i.e. the material is characterized by having a low modulus. As discussed above, it is also important that the device be deformable to fit in the introducer and also be capable of unfolding or expanding in the blood vessel. Such materials can be made from natural biopolymers or from synthetic materials that degrade into harmless components within a living tissue. Examples of materials may be various natural biopolymers, pure or chemically manipulated, based on alginic acid, hyalauronic acid or chitosan. Examples of soft and flexible synthetic absorbable polymers are aliphatic polyurethanes, polyphospazenes and polyorthoesters and those polymers made from glycolide, lactide, caprolactone, trimethylene carbonate, butyrolactone, 1,4-dioxan-2-one or 1,5-dioxepan-2-one. Yet another way to achieve a soft and flexible material is the use of plasticizers to bring down the glass transition temperature of the material.

As described above, soft and flexible absorbable materials normally have a low rupture strength, which, in turn, means that there is a potential risk that a fastening means, such as a multifilament or a suture, is torn lose by rupturing through the sealing device. During the implantation procedure, the doctor needs to feel that the sealing device is pulled in close apposition to the vessel wall. During this procedure the surgeon needs to pull with some force, which is applied with great individual variability, that will be transmitted through the fastening means and act on the sealing device. In the present case, without the invention, there is therefore a potential risk that a multifilament saws its way through the material in the sealing device between two through holes, thereby leaving the sealing device loose inside the vessel. In order to overcome this potentially severe problem, the area around and between the two through holes has been reinforced with a second material having higher rupture strength.

The low modulus absorbable materials may be formed into any desired shape by any thermoforming method like compression or injection moulding and by casting of a polymer solution. If the moulds used to form the article have protrusions or elevated shapes that will leave certain areas of the article unfilled or partly filled with material during the moulding or casting operation, this will leave indentations, such as grooves, channels or through openings in the article, that can be filled with a second material characterized by having a higher strength that will resist the fastening means from being torn loose or rupturing through the first soft and flexible material. These indentations may have any desired shape, depth or area, and the depth may be less or equal to the thickness of the moulded article.

Such an indentation or opening may be filled with another, second material, in a second moulding operation or in the same moulding operation but preferably after the first material has crystallized or attained its final shape and properties. The second material can also be formed in a separate process and placed into the first formed material. The second material is typically made from a synthetic absorbable material having a glass transition temperature above the normal body temperature or a melting point above 50° C. Examples of such materials are polymers or copolymers made predominately from glycolide, lactide, or butyrolactone and can furthermore comprise trimethylene carbonate, caprolactone, 1,4-dioxan-2-one or 1,5-dioxepan-2-one.

In FIG. 1 is shown a portion of a vessel 1 in a living body, such as the femoral artery. A puncture has been made through the vessel wall 2, thereby creating an opening, which has to be occluded after the treatment that made the puncture necessary. In FIG. 1, a first embodiment of a wound closure device according to the present invention has been positioned to close the puncture wound. The wound closure device comprises a first sealing device 3, which is positioned against the inner surface of the vessel wall 2, and a second sealing device 4, which is positioned against the outer surface of the vessel wall 2. The wound closure device comprises also a fastening means 5 in the form of a multifilament 5, which holds the first and second sealing devices 3, 4 together by means of friction locking. As is best seen in FIG. 2, the first sealing device 3 comprises also recesses in the forms of two through holes 6 and 7, through which the multifilament 5 is to be threaded.

Figure 2:
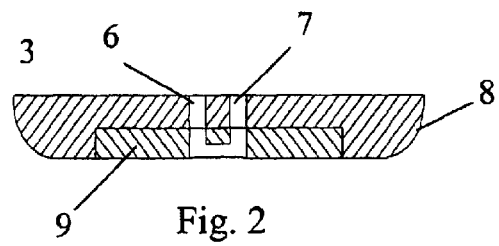
FIG. 2 shows a cross-section of the inner sealing device of the wound closure device of FIG. 1.
Figure 3:
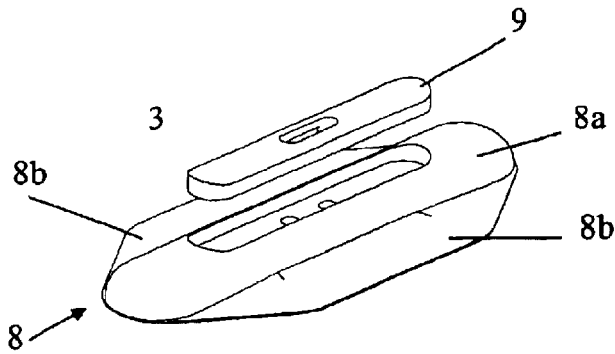
FIG. 3 illustrates an inventive sealing device together with a separate reinforcement insert.
Figure 4:
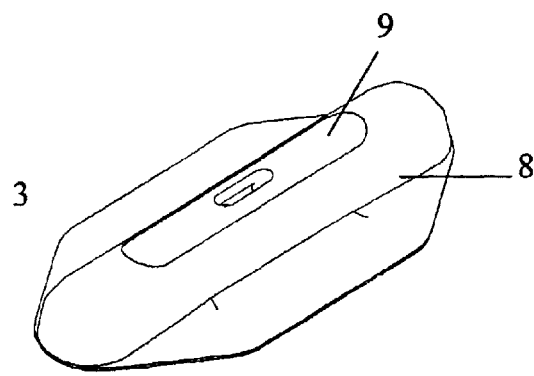
FIG. 4 illustrates the sealing device of FIG. 3, with the reinforcement insert being an integral part of the sealing device.

As is indicated in FIG. 2 and more clearly seen in FIG. 3, the sealing device 3 comprises a base portion 8, which is made of a material having a low modulus, and a reinforcement portion 9, which is made of a material having a higher modulus. The base portion 8 comprises an elongated comparatively stiff central portion 8a and flexible side wings 8b which are substantially thinner than the central portion 8a. In FIG. 3, the reinforcement portion 9 is illustrated as a separate reinforcement insert 9 to the base portion 8. In praxis, and as is shown in FIG. 4, the reinforcement portion 9 can be provided as an integral part of the base portion 8 by means of some of the casting or moulding techniques described above. The provision of a reinforcement portion 9 considerably enhances the overall rupture strength of the sealing device 3. As an example, when the material in the base portion 8 of the sealing device 3 is a segmented copolymer made from glycolide, ε-caprolactone and trimethylene carbonate with a small volume of poly-d,l-lactide-co-glycolide (or a polymer comprising at least 70% lactide units) moulded into the reinforcement part 9, the force required to pull the multifilament 5 through the sealing device 3 is about 35 N, whereas this force—with otherwise the same design of the sealing device 3—is about 18 N when the reinforcement portion 9 of poly-d,l-lactide-co-glycolide is omitted.

Figure 5:
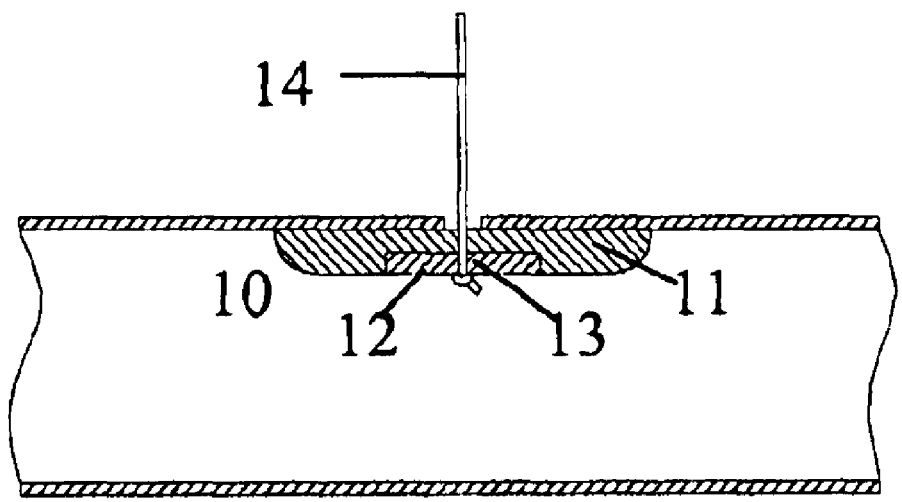
FIG. 5 is a schematic illustration of second embodiment of a sealing device according to the present invention.

A second embodiment of a wound closure device according to the present invention is shown in FIG. 5. This wound closure device comprises a sealing device 10, which comprises a base portion 11 and, in its centre, a reinforcement portion 12. The reinforcement portion 12 is provided to increase the rupture strength of the sealing device 10. A recess 13 in the form of a single through hole 13 is provided in the centre of the reinforcement portion 12. Through this through hole 13 a retracting or fastening means 14 in the form of a suture 14 can be passed and secured with a knot, a drop of an adhesive or melted plastic, or similar. It is not necessary that the hole 13 pass all the way through the base portion 11. Instead, the hole could end inside the reinforcement portion 12, so that the suture 14 is secured within the sealing device 10. In use, the sealing device 10 is urged toward the inner surface of a vessel wall by simply pulling the suture 14.

Figure 6:
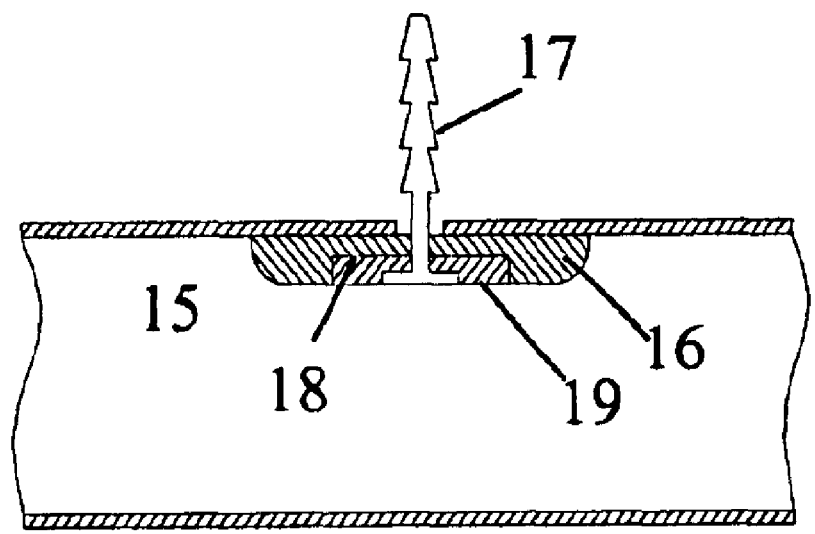
FIG. 6 is a schematic illustration of a third embodiment of a sealing device according to the present invention.

FIG. 6 illustrates a third embodiment of a wound closure device. The wound closure device in FIG. 6 comprises a sealing device 15, which comprises a base portion 16 and a fastening means 17 in the form of a stem 17, which has a saw-tooth profile for mating with an outer locking seal (not shown). The stem 17 has an enlarged base, which is anchored within a recess 18 in the sealing device 15; and in order to enhance the rupture strength of the sealing device 15, the recess 18 is filled with a material having a higher modulus, thereby providing a reinforcement portion 19 around the base of the stem 17.

Although the present invention has been described with reference to specific embodiments, also shown in the appended drawings, it will be apparent for those skilled in the art that many variations and modifications can be done within the scope of the invention as described in the specification and defined in the following claims. Accordingly, it should be noted that the sealing devices according to the present invention might adopt several different embodiments. In particular, it should be noted that recesses for fastening means may be provided in the form of holes (as in FIG. 2 to FIG. 5), which may go through the whole sealing device and the edges or walls of which are provided with a material having a higher modulus, or the recess can be provided in the form of a cavity (as in FIG. 6), which is filled with a material having a higher modulus, thereby creating reinforcement for a fastening means secured inside this cavity. Furthermore, it should be noted that the fastening means may be provided as a separate part of a sealing device, e.g. in the form of a suture or a multifilament which runs through or into the sealing device, or the fastening means may be an integrated part of the sealing device (as in FIG. 6).

Although the present invention has been described with reference to specific embodiments, also shown in the appended drawings, it will be apparent for those skilled in the art that many variations and modifications can be done within the scope of the invention as described in the specification and defined in the following claims. For example, one, two, or more than two (for example three or four) through holes may be provided. Accordingly, the examples shown below are merely provided to illustrate the invention and should not be considered to limit the invention.

EXAMPLES

Below the present invention will be further described by a set of non-limiting examples.

Example 1

A triaxial segmented copolymer where the soft segments is polymerized from a mixture of caprolactone, trimethylene carbonate and glycolide and the hard segments consist of glycolide and is compression moulded at 198° C. to form an article as shown in FIG. 4. A multifilament is put through the holes moulded into the article. The article is mounted under a slotted metal bar clamped into the lower grip of a universal testing machine, and the multifilament is clamped in the upper grip. The grips are separated with a speed of 100 mm/min, and the force required for the multifilament to rupture through the article is recorded. The mean value of 5 tested articles is 18 N.

Example 2

The same copolymer as in Example 1 was moulded at 198° C. in a slightly different mould having an indentation making a groove into the moulded article as can be seen in the cross sectional drawing in FIG. 2. In a second moulding operation, pellets of poly-d,l-lactide was placed into one of the mould halves together with the first moulded article and the mould was heated to 140° C. before load was applied over the mould halves for 2 minutes. The moulds were cooled and the article was removed. The grove in the first moulded article was completely filled with the poly-d,l-lactide and a multifilament was passed through the holes and the force to pull out the multifilament was measured as in Example 1. The mean value of 5 tested articles was 35 N.

Example 3

Same procedure as in Example 2 above, but poly-d,l-lactide was exchanged with other absorbable materials and processed at different temperatures. Results from mechanical testing are shown in the table below.

| First material | Second material | Rupture strength |
| --- | --- | --- |
| poly-GA/CL/TMC | N/A | 18 N |
| poly-GA/CL/TMC | poly-GA/LA, i.v 1.0 | 34 N |
| poly-GA/CL/TMC | poly-GA/LA, i.v 2.5 | 39 N |
| poly-GA/CL/TMC | poly-l-LA/d, l-LA | 35 N |
| poly-GA/CL/TMC | poly-l-LA/TMC | 35 N | where GA is glycolide, CL is ε-caprolactone, TMC is trimethylene carbonate, l-LA is l,l-lactide and d,l is d,l-lactide units in the polymer.

What is claimed is:

1. Absorbable medical sealing device for closing a wound in a vessel, wherein the sealing device comprises a base portion, which is made of a first material having a lower Young's modulus, and a reinforcement portion, which is made of a second material having a higher Young's modulus, wherein said reinforcement portion is configured to reinforce said base portion, and wherein the base portion comprises a central portion and flexible side wings substantially thinner than the central portion and adapted so that, after application of the sealing device to the wound, a face of the base portion conforms to and is substantially in contact with an inner surface of the vessel so that it covers and seals the wound.

2. Absorbable medical sealing device according to claim 1, further comprising recesses, wherein recesses are in the form of at least two through holes, through which a fastener is threaded in at least one loop, wherein the at least two through holes pass through the reinforcement portion, so that the portion of the sealing device which is between the at least two through holes is reinforced with the second material.

3. Absorbable medical sealing device according to claim 1, wherein the reinforcement portion is provided as an integral part of the sealing device.

4. Absorbable medical sealing device according to claim 1, further comprising a recess, wherein the recess is in the form of a through hole, through which a fastener is threaded and secured at the opposite side, wherein the through hole goes through the reinforcement portion, so that the wall of the through hole is reinforced with the second material.

5. Absorbable medical sealing device according to claim 1, further comprising a recess, wherein the recess is in the form of an opening into which a fastener is inserted, wherein said opening ends inside the reinforcement portion, so that the fastener is secured within the reinforcement portion.

6. Absorbable medical sealing device according to claim 1, further comprising one of a multifilament and a suture.

7. Absorbable medical sealing device according to claim 1, wherein the material in the base portion is a segmented polymer made from at least one of glycolide, ε-caprolactone and trimethylene carbonate, wherein a small volume of a polymer comprising at least 70% lactide units is molded into the reinforcement portion.

8. Absorbable medical sealing device according to claim 7, wherein said lactide units are l-lactide.

9. Absorbable medical sealing device according to claim 1, further comprising a fastener secured to the reinforcement portion.

10. Absorbable medical sealing device for closing a wound in a vessel, wherein the sealing device comprises a base portion, which is made of a first material having a lower Young's modulus, and a reinforcement portion, which is made of a second material having a higher Young's modulus, wherein the reinforcement portion is provided as a separate insert to the sealing device and configured to be inserted into the base portion, and wherein the base portion comprises a central portion and the insert is located only in the central portion and away from a peripheral portion of the sealing device.

11. Absorbable medical sealing device for closing a wound in a vessel, wherein the sealing device comprises a base portion, which is made of a first material having a lower Young's modulus, and a reinforcement portion, which is made of a second material having a higher Young's modulus, wherein the reinforcement portion is a recess in the base portion, which recess is filled with the second material, and a fastener is provided in the form of a stem, the base of which is secured within the reinforcement portion.

12. Absorbable medical sealing device for closing a wound in a vessel, wherein the sealing device comprises a base portion, which is made of a first material having a lower Young's modulus, and a reinforcement portion, which is made of a second material having a higher Young's modulus, wherein said reinforcement portion is configured to reinforce said base portion, and wherein the base portion and reinforcement portion are configured so that, after application of the sealing device to the wound, one face of the base portion is substantially in contact with an inner surface of the vessel and an opposite face of the base portion is substantially in contact with the reinforcement portion.

* * * * *